Dec. 8, 1936. G. E. LUKENS Plant Pat. 209
ROSE
Filed June 13, 1936
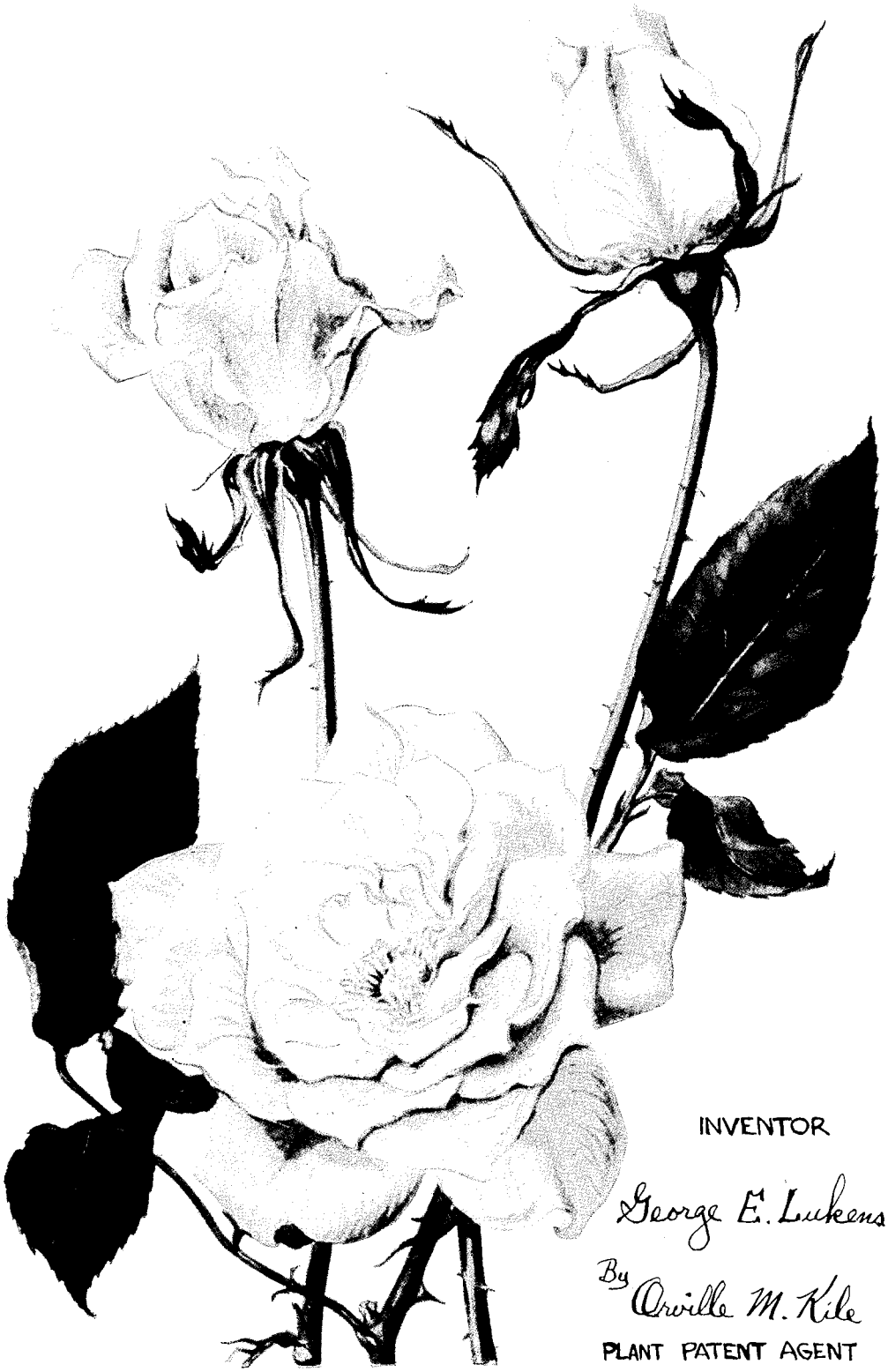
INVENTOR
George E. Lukens
By Orville M. Kile
PLANT PATENT AGENT Patented Dec. 8, 1936 Plant Pat. 209

UNITED STATES PATENT OFFICE

209

ROSE

George E. Lukens, North Wales, Pa., assignor to The Florex Gardens, North Wales, Pa., a corporation of Pennsylvania Application June 13, 1936, Serial No. 85,143

1 Claim. (Cl. 47—61)

My present invention relates to a new and improved variety of hybrid tea rose plant, involving novel and interesting color effects and other desirable qualities.

This new variety is a sport of Talisman and has been reproduced through several generations so that its qualities have been proved permanently fixed.

The accompanying illustration shows a bud, a half-open flower and a fully opened flower, together with foliage and stems—all depicted as nearly as possible in their true form and colors.

The following is a detailed description of this new variety of rose and the color references are to Ridgway's Color Standards and Nomenclature.

*The plant*

*Form.*—Bush, upright, of moderate height.

*Habits of growth.*—Has usual Talisman characteristics. Vigorous grower, disease resistant.

Foliage:

*Leaves.*—Compound; of three or five leaflets. Abundant.

*Leaflets.*—Oval in shape, pointed. Large—the terminal leaflet of each leaf measures from 3¼ to 3½ inches in length and 1½ or more inches in width. Rather flat and not given to crinkling. Margin evenly and moderately serrate.

*Color.*—Dark Cress Green (Plate XXXI) on upper side; Light Elm Green (Plate XVII) on under side.

*Rachis.*—Smooth.

*Stipules.*—Wide, sharp pointed.

*Stems.*—Long and strong. Olive Green (Plate IV).

*Thorns.*—Large, long, straight pinkish thorns pointing slightly downward. Occur irregularly and rather numerously. Many spines on peduncle.

*Sepals.*—Long, slightly inclined to be foliaceous; recurve moderately. Outside green and smooth; inside very light green and hairy.

*Reproductive organs*

*Stamens.*—Many.

*Filaments.*—Brown, extending slightly above pistil.

*Anthers.*—Brown, attached to filament at end and standing almost vertical.

*Pistils.*—Numerous.

*Styles.*—Many, white.

*Stigmas.*—Light yellow.

*Ovaries.*—Enclosed.

*Hips.*—Large, globular, Cress Green (Plate XXXI).

*Flower*

Bud:

*Size.*—About 2 inches long.

*Shape.*—Ovoid.

*Peduncle.*—Long, heavy, erect, bearing many spines.

*Color.*—Dark Rose Color (Plate XII).

*Opening.*—Opens slowly and evenly.

Bloom:

*Size.*—Large—5 inches across.

*Form.*—Full and flat centered; does not recurve or quill; stamens usually covered; retains its shape.

*Petalage.*—Double, having in the month of March in the inventor's greenhouses, about 35 petals.

*Color.*—When first open the general tonal effect of the rose is Peach Red (Plate I) with a Rose Color frame produced by the outer row of petals (Plate XII). When older the general effect is slightly darker than Rose Color (Plate XII).

The inside of the petals of the outer row is Rose Color (Plate XII) at the tip, deepening in shade toward the middle of the petal. The under side of these petals is slightly darker. There is a large, bright spot of Lemon Chrome (Plate IV) at the base of the outside of each petal and this diffuses upward into the Rose Color, also forms a line up the middle almost to the top of the petal. The veining on the outside of the outer petals is rather prominent.

The intermediate petals carry more of the Coral hue and are nearly Rose Doree (Plate I) on the outside although they have slightly more of the Yellow suffusion than is shown in Rose Doree. The inside of the intermediate petals approaches Light Coral Red (Plate XIII).

The small inner petals are Strawberry Pink (Plate I) on the inside and outside they are Rose Doree (Plate I).

As the open flower ages it darkens decidedly—the outer petals becoming Tyrian Rose (Plate XII) and the inner petals taking on more of the Rose Color, the inside being Peach Red (Plate I) and the outside Begonia Rose (Plate I).

Petals:

*Substance.*—Thick.

*Arrangement.*—Imbricated; close.

*Shape.*—Almost round with terminal point.

*Persistence.*—Cling tenaciously until dry.

*Fragrance.*—Strong, pleasant and lasting.

*Longevity.*—Particularly long-lived, probably due to its slow opening.

*Comparisons*

The new variety is readily distinguishable from its parent—Talisman—because of the distinctive coloring as described. It also has a larger bloom than has Talisman, carrying a greater number of petals.

Having thus disclosed my invention, what I claim as new is:

The variety of rose as described, characterized particularly by the distinct color of its large fragrant bloom; its excellent keeping qualities; its vigorous growth and abundance of rich foliage; and its long, strong stems.

GEORGE E. LUKENS.